United States Patent
Bae et al.

(10) Patent No.: US 9,916,845 B2
(45) Date of Patent: *Mar. 13, 2018

(54) METHOD FOR DETERMINING ALCOHOL USE BY COMPARISON OF HIGH-FREQUENCY SIGNALS IN DIFFERENCE SIGNAL, AND RECORDING MEDIUM AND DEVICE FOR IMPLEMENTING SAME

(71) Applicant: Foundation of Soongsil University-Industry Cooperation, Seoul (KR)

(72) Inventors: Myung Jin Bae, Seoul (KR); Sang Gil Lee, Busan (KR); Seong Geon Bae, Seoul (KR)

(73) Assignee: FOUNDATION OF SOONGSIL UNIVERSITY—INDUSTRY COOPERATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/300,168

(22) PCT Filed: Apr. 2, 2014

(86) PCT No.: PCT/KR2014/002849
§ 371 (c)(1),
(2) Date: Sep. 28, 2016

(87) PCT Pub. No.: WO2015/147362
PCT Pub. Date: Oct. 1, 2015

(65) Prior Publication Data
US 2017/0140776 A1    May 18, 2017

(30) Foreign Application Priority Data
Mar. 28, 2014  (KR) ........................ 10-2014-0036602

(51) Int. Cl.
*G10L 25/00*    (2013.01)
*G10L 25/66*    (2013.01)
(Continued)

(52) U.S. Cl.
CPC ............ *G10L 25/66* (2013.01); *A61B 5/4845* (2013.01); *A61B 5/7257* (2013.01);
(Continued)

(58) Field of Classification Search
CPC ......... G10L 25/66; G10L 25/21; G10L 25/15; G10L 17/26; G10L 15/00; G10L 15/02;
(Continued)

(56) References Cited

U.S. PATENT DOCUMENTS 5,450,525 A * 9/1995 Russell ............... B60R 16/0373
704/275
5,704,008 A * 12/1997 Duvall, Jr. .............. B60R 25/04
704/273

(Continued)

FOREIGN PATENT DOCUMENTS

EP    1850328 A1    10/2007
JP    2003-36087 A    2/2003
(Continued)

OTHER PUBLICATIONS

See-Woo Lee, "A Study on Formant Variation with Drinking and Nondrinking Condition," Department of Information & Telecommunication Engineering, Sangmyung University, vol. 10, No. 4, pp. 805-810, 2009.

(Continued)

*Primary Examiner* — Abdelali Serrou
(74) *Attorney, Agent, or Firm* — Sang Ho Lee; Novick, Kim & Lee, PLLC

(57) ABSTRACT

This method for determining alcohol use comprises the steps of: detecting an effective frame in an input audio signal;

(Continued)

detecting a difference in signal within the original signal of the effective frame; performing a fast Fourier conversion on the difference signal to be transformed into a frequency domain; detecting high-frequency components within the difference signal subjected to the fast Fourier transform; and determining the state of alcohol use on the basis of a gradient difference between the high-frequency components. Accordingly, the present invention can identify the state and extent of alcohol use by a driver or an operator from a long distance and thus can prevent accidents caused by driving or operating vehicles and machines under the influence of alcohol.

20 Claims, 6 Drawing Sheets

(51) Int. Cl.
  *G10L 25/93* (2013.01)
  *G10L 25/30* (2013.01)
  *G10L 25/21* (2013.01)
  *A61B 5/00* (2006.01)
  *A61B 7/00* (2006.01)
(52) U.S. Cl.
  CPC .............. *A61B 5/7264* (2013.01); *A61B 7/00* (2013.01); *G10L 25/21* (2013.01); *G10L 25/30* (2013.01); *G10L 25/93* (2013.01)
(58) Field of Classification Search
  CPC ......... G10L 15/20; G10L 25/12; G10L 25/09; G10L 25/06; G10L 25/03; G10L 25/60; G10L 25/63; G10L 25/07
  See application file for complete search history.

(56) References Cited

U.S. PATENT DOCUMENTS

| | | | | |
|---|---|---|---|---|
| 5,719,950 | A * | 2/1998 | Osten | A61B 5/1171 340/5.82 |
| 5,774,858 | A * | 6/1998 | Taubkin | B60R 25/257 704/270 |
| 5,776,055 | A | 7/1998 | Hayre | |
| 5,913,188 | A | 6/1999 | Tzirkel-Hancock | |
| 5,983,189 | A * | 11/1999 | Lee | G08B 21/06 704/273 |
| 6,006,188 | A | 12/1999 | Bogdashevsky | |
| 6,205,420 | B1 | 3/2001 | Takagi | |
| 6,236,968 | B1 * | 5/2001 | Kanevsky | G08B 21/06 704/270 |
| 6,275,806 | B1 | 8/2001 | Pertrushin | |
| 6,446,038 | B1 | 9/2002 | Bayya | |
| 6,748,301 | B1 * | 6/2004 | Ryu | B60K 28/063 340/426.11 |
| 7,925,508 | B1 | 4/2011 | Michaelis | |
| 7,962,342 | B1 * | 6/2011 | Coughlan | G10L 15/22 379/201.01 |
| 8,478,596 | B2 * | 7/2013 | Schultz | G10L 17/26 704/200 |
| 8,938,390 | B2 | 1/2015 | Xu | |
| 9,058,816 | B2 | 6/2015 | Lech | |
| 9,659,571 | B2 | 5/2017 | Van Der Schaar | |
| 9,672,809 | B2 | 6/2017 | Togawa et al. | |
| 2002/0010587 | A1 | 1/2002 | Pertrushin | |
| 2002/0194002 | A1 | 12/2002 | Pertrushin | |
| 2003/0069728 | A1 | 4/2003 | Tato | |
| 2004/0167774 | A1 | 8/2004 | Shrivastav | |
| 2005/0075864 | A1 | 4/2005 | Kim | |
| 2005/0102135 | A1 | 5/2005 | Goronzy | |
| 2007/0071206 | A1 | 3/2007 | Gainsboro | |
| 2007/0124135 | A1 * | 5/2007 | Schultz | G10L 17/26 704/201 |
| 2007/0192088 | A1 | 8/2007 | Oh | |
| 2007/0213981 | A1 | 9/2007 | Meyerhoff | |
| 2007/0288236 | A1 | 12/2007 | Kim | |
| 2009/0265170 | A1 | 10/2009 | Irie et al. | |
| 2010/0010689 | A1 | 1/2010 | Yasushi et al. | |
| 2011/0035213 | A1 | 2/2011 | Malenovsky | |
| 2011/0282666 | A1 | 11/2011 | Washio | |
| 2012/0089396 | A1 | 4/2012 | Patel | |
| 2012/0116186 | A1 | 5/2012 | Shrivastav | |
| 2012/0262296 | A1 | 10/2012 | Bezar | |
| 2013/0006630 | A1 | 1/2013 | Hayakawa | |
| 2013/0253933 | A1 * | 9/2013 | Maruta | G10L 15/00 704/246 |
| 2014/0122063 | A1 | 5/2014 | Gomez Vilda | |
| 2014/0188006 | A1 | 7/2014 | Alshaer | |
| 2014/0379348 | A1 | 12/2014 | Sung | |
| 2015/0127343 | A1 | 5/2015 | Mullor et al. | |
| 2015/0257681 | A1 | 9/2015 | Shuster et al. | |
| 2015/0310878 | A1 | 10/2015 | Bronakowski | |
| 2015/0351663 | A1 | 12/2015 | Zigel | |
| 2016/0155456 | A1 | 6/2016 | Wang | |
| 2016/0379669 | A1 | 12/2016 | Bae et al. | |
| 2017/0004848 | A1 | 1/2017 | Bae et al. | |

FOREIGN PATENT DOCUMENTS

| | | |
|---|---|---|
| JP | 2010-015027 A | 1/2010 |
| JP | 5017534 B2 | 9/2012 |
| KR | 10-1997-0038004 A | 7/1997 |
| KR | 10-0201256 B1 | 6/1999 |
| KR | 10-0206205 B1 | 7/1999 |
| KR | 1999-0058415 A | 7/1999 |
| KR | 10-2004-0033783 A | 4/2004 |
| KR | 10-0497837 B1 | 6/2005 |
| KR | 10-0664271 B1 | 1/2007 |
| KR | 10-2009-0083070 A | 8/2009 |
| KR | 10-2012-0074314 A | 7/2012 |
| WO | 2012/014301 A1 | 2/2012 |

OTHER PUBLICATIONS

Jung, Chan Joong et al. "A Study on Detecting Decision Parameter about Drinking in Time Domain," The Journal of Korea Information and Communications Society (winter) 2014, pp. 784-785, Jan. 2013.

Seong Geon Bae, Dissertation for Ph.D, "A study on Improving Voice Surveillance System Against Drunk Sailing". Information and Communication Engineering Dept., Soongsil University, Republic of Korea. Dec. 2013 (English Abstract at pp. x-xii).

Bocklet, Tobias, Korbinian Riedhammer, and Elmar Noth. "Drink and Speak: On the automatic classification of alcohol intoxication by acoustic, prosodic and text-based features." Twelfth Annual Conference of the International Speech Communication Association. 2011.

Tae-Hun Kim et al. "Drinking Speech System", Department of Information Communication, Sang Myung University, Nov. 2006, pp. 257-262.

Seong-Geon Bae et al. "A Study on Personalized Frequency Bandwidth of Speech Signal using Formant to LPC," The Journal of Korean Institute of Communications and Information Sciences (winter), 2013, pp. 669-670.

Seong-Geon Bae et al. "A Study on Drinking Judgement Method of Speech Signal Using the Fomant Deviation in the Linear Prediction Coefficient," he Journal of Korean Institute of Communications and Information Sciences (winter), 2013, pp. 667-668.

Lee, Won Hui et al. "Valid-frame Distance Deviation of Drunk and non-Drunk Speech" The Journal of Korea Information and Communications Society (winter) 2014, pp. 876-877, Jan. 2014.

Lee, Won-Hee et al.."A Study on Drinking Judgement using Differential Signal in Speech Signal", The Journal of Korea Information and Communications Society (winter) 2014, pp. 878-879, Jan. 2014.

Geumran Baek et al. "A Study on Voice Sobriety Test Algorithm in a Time-Frequency Domain" International Journal of Multimedia and Ubiquitous Engineering vol. 8 No. 5 (2013), pp. 365-402.

(56) References Cited

OTHER PUBLICATIONS

Chan Joong Jung et al. "A Study on Drunken Decision using Spectral Envelope Changes" Korea Institute of Communications and Information Sciences, Winter Conference, vol. 2013 No. 1 (2013), pp. 674-675.
Chan Joong Jung et al. "Speech Sobriety Test Based on Formant Energy Distribution" International Journal of Multimedia and Ubiquitous Engineering vol. 8 No. 6 (2013), pp. 209-216.
Baumeister, Barbara, Christian Heinrich, and Florian Schiel. "The influence of alcoholic intoxication on the fundamental frequency of female and male speakers." The Journal of the Acoustical Society of America 132.1 (2012): 442-451.
Schuller, Bjorn W., et al. "The INTERSPEECH 2011 Speaker State Challenge." INTERSPEECH. 2011.
Hollien, Harry, et al. "Effects of ethanol intoxication on speech suprasegmentals." The Journal of the Acoustical Society of America 110.6 (2001): 3198-3206.
Kim (Kim, Jonathan, Hrishikesh Rao, and Mark Clements. "Investigating the use of formant based features for detection of affective dimensions in speech." Affective computing and intelligent interaction (2011): 369-377.).
Broad (Broad, David J., and Frantz Clermont. "Formant estimation by linear transformation of the LPC cepstrum." The Journal of the Acoustical Society of America 86.5 (1989)).
Sato (Sato, Nobuo, and Yasunari Obuchi. "Emotion recognition using mel-frequency cepstral coefficients." Information and Media Technologies 2.3 (2007): 835-848.).

\* cited by examiner

METHOD FOR DETERMINING ALCOHOL USE BY COMPARISON OF HIGH-FREQUENCY SIGNALS IN DIFFERENCE SIGNAL, AND RECORDING MEDIUM AND DEVICE FOR IMPLEMENTING SAME

TECHNICAL FIELD

The present invention relates to a method of determining whether alcohol has been consumed and a recording medium and device for implementing the same, and more particularly, the invention relates to a method of determining whether alcohol has been consumed by using a method of comparing high-frequency signals in a difference signal using voice, and a recording medium and device for implementing the same.

BACKGROUND ART

Although consuming a moderate amount of alcohol offers various benefits to people, excessive consumption is harmful to health. In addition, drunk driving causes fatal accidents and, in some cases, even death.

As for methods of measuring drunkenness, there is a method of measuring the concentration of alcohol in exhaled air during respiration using a breathalyzer equipped with an alcohol sensor and there is a method of measuring the concentration of alcohol in the blood flow using a laser. Generally, the former method is usually used for cracking down on drunk driving. In this case, when any driver refuses a sobriety test, the Widmark Equation may be used to estimate a blood alcohol concentration by collecting the blood of the driver with his or her consent.

Accidents caused by operating a vehicle under the influence of alcohol at sea or in the air, in addition to vehicular accidents, are also problematic. However, an existing alcohol consumption measurement method requires testing the operator in person and thus, is not suitable for determining whether an operator at a remote location is drunk.

Accordingly, the government is exerting various efforts to prevent operating a vehicle under the influence of alcohol at sea or in the air. As one of the efforts, for a vessel, controlling the number of individuals who are operating vehicles under the influence of alcohol is performed by measuring alcohol consumption before and after operation. However, the measurement is difficult during the time the individual is actively operating the vehicle. In some cases, the Coast Guard may perform random sobriety checks through direct contact at sea. However, this method is very dangerous due to the difficulty of making vessel-to-vessel contact and a flight risk from the vessel.

Accordingly, determining whether alcohol has been consumed is indirectly ascertained via communication with an operator at sea. However, it is difficult to determine whether alcohol has been consumed when the operator denies drinking alcohol. Thus, there is a need for a method of indirectly and objectively determining whether an operator, even from a long distance, has consumed alcohol.

DISCLOSURE

Technical Problem

The present invention is directed to providing an alcohol consumption determination method for determining whether alcohol has been consumed and the degree of the consumption by analyzing an operator's voice taken over communication.

The present invention is also directed to providing a recording medium having a computer program recorded thereon for performing the alcohol consumption determination method.

The present invention is also directed to providing a device for performing the alcohol consumption determination method.

Technical Solution

According to an embodiment for achieving the above-described objective of the present invention, an alcohol consumption determination method includes detecting an effective frame of an input voice signal; detecting a difference signal of an original signal of the effective frame; converting the difference signal into a frequency domain signal by performing a fast Fourier transform on the difference signal; detecting high-frequency components of the fast-Fourier-transformed difference signal; and determining whether alcohol has been consumed based on slope differences among the high-frequency components.

Determining whether alcohol has been consumed may include generating frequency slopes of the high-frequency components; measuring slope differences among the high-frequency components to measure energy differences among the high-frequency components; adding up the measured energy differences to calculate an average of the energy differences; and determining that alcohol has been consumed when the average is greater than a threshold and outputting a result of the determination.

Each of the frequency slopes of the high-frequency components may be a formant slope.

The measuring of slope differences among the high-frequency components to measure energy differences among the high-frequency components may include measuring slope differences among neighboring high-frequency components.

The detecting of an effective frame may include forming a voice frame of the input voice signal; and determining whether the voice frame corresponds to a voiced sound.

The detecting of high-frequency components of the fast-Fourier-transformed difference signal may include sequentially grouping the detected high-frequency components in sets of four.

The detecting of a difference signal may include generating a shift signal $S(n-1)$ by shifting the original signal $S(n)$ of the effective frame; and outputting a difference signal $S(n)-S(n-1)$ between the original signal and the shift signal.

According to an embodiment for achieving the above-described other objective of the present invention, there is a computer-readable recording medium having a computer program recorded thereon for performing the above-described alcohol consumption determination method.

According to an embodiment for achieving the above-described still other objective of the present invention, an alcohol consumption determination device includes: an effective frame detection unit configured to detect an effective frame of an input voice signal; a difference signal detection unit configured to detect a difference signal of an original signal of the effective frame; a Fourier transform unit configured to convert the difference signal into a frequency domain signal by performing a fast Fourier transform on the difference signal; a high-frequency detection unit configured to detect high-frequency components of the fast-Fourier-transformed difference signal; and an alcohol consumption determination unit configured to determine whether alcohol has been consumed based on slope differences among the high-frequency components.

The alcohol consumption determination unit may include a slope extraction unit configured to generate frequency slopes of the high-frequency components; an energy difference detection unit configured to measure slope differences among the high-frequency components to measure energy differences among the high-frequency components; an average calculation unit configured to add up the measured energy differences to calculate an average of the energy differences; and a result output unit configured to determine that alcohol has been consumed when the average is greater than a threshold and output a result of the determination.

Each of the frequency slopes of the high-frequency components may be a formant slope. The energy difference detection unit may measure slope differences among neighboring high-frequency components.

The effective frame detection unit may include: a frame forming unit configured to form a voice frame of the input voice signal; and a voiced sound determination unit configured to determine whether the voice frame corresponds to a voiced sound.

The high-frequency detection unit may include a first high-frequency detection unit configured to detect (4n−3)th high-frequency components (where, n is a natural number) of the fast-Fourier-transformed difference signal; a second high-frequency detection unit configured to detect (4n−2)th high-frequency components of the fast-Fourier-transformed difference signal; a third high-frequency detection unit configured to detect (4n−1)th high-frequency components of the fast-Fourier-transformed difference signal; and a fourth high-frequency detection unit configured to detect (4n)th high-frequency components of the fast-Fourier-transformed difference signal.

The difference signal detection unit may include a shift signal unit configured to generate a shift signal S(n−1) by shifting the original signal S(n) of the effective frame; and a difference signal output unit configured to output a difference signal S(n)−S(n−1) between the original signal and the shift signal.

Advantageous Effects

According to the present invention, it is possible to determine whether a driver or an operator at a remote location has consumed alcohol and the degree of the consumption, and apply voices before and after drinking to those that are speaker independent and speaker dependent by comparing, analyzing, and extracting a feature parameter of a voice and a high-frequency component in the frequency domain. In particular, it is also possible to divide a change in voice for one frame into small units, measure a change in the high frequency, and use the measured change as a feature parameter. Thus, the present invention is useful in measuring a short-term change in voice.

Accordingly, it is also possible to extract a voice of a driver or an operator at a remote location over communication to indirectly and objectively determine whether alcohol has been consumed, thus preventing an accident caused by a drunk operation.

MODES FOR CARRYING OUT THE INVENTION

Figure 1:
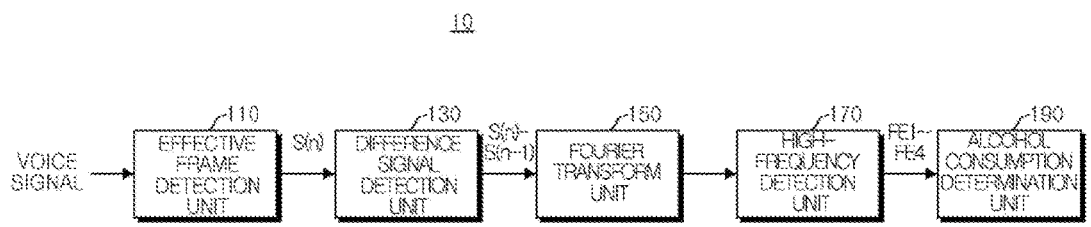
FIG. 1 is a block diagram showing a device for determining alcohol consumption according to an embodiment of the present invention.

The following detailed description refers to the accompanying drawings that illustrate exemplary embodiments consistent with the present invention. These embodiments will be described in sufficient detail to enable those skilled in the art to practice the present invention. It is to be understood that the various embodiments of the present invention, although different, are not necessarily mutually exclusive. For example, a particular feature, structure or characteristic described herein in connection with one embodiment may be implemented within other embodiments without departing from the spirit and scope of the present invention. In addition, it is to be understood that the location or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar elements throughout the several views.

Hereinafter, preferred embodiments of the present invention will be described in more detail with reference to the accompanying drawings.

FIG. 1 is a block diagram showing a device for determining alcohol consumption according to an embodiment of the present invention.

Referring to FIG. 1, a device 10 for determining alcohol consumption according to an embodiment includes an effective frame detection unit 110 configured to detect an effective frame of an input voice signal, a difference signal detection unit 130 configured to detect a difference signal of an original signal of the effective frame, a Fourier transform unit 150 configured to convert the difference signal into the frequency domain by performing a fast Fourier transform on the difference signal, a high-frequency detection unit 170 configured to detect high-frequency components of the difference signal on which the fast Fourier transform is performed, and an alcohol consumption determination unit 190 configured to determine whether alcohol has been consumed on the basis of slope differences among the high-frequency components.

Alcohol consumption determination software (application) may be installed and executed in the device 10 according to the present invention. Elements such as the effective frame detection unit 110 may be controlled by the alcohol consumption determination software executed in the device 10.

The device 10 may be a separate terminal or a module of a terminal. The device 10 may be fixed or may have mobility. The device 10 may be referred to by other terms such as a terminal, a user equipment (UE), a mobile station (MS), a mobile terminal (MT), a user terminal (UT), a subscriber station (SS), a wireless device, a personal digital assistant (PDA), a wireless modem, a handheld device, or the like.

The device 10 may support wired or wireless communication and may include an electronic device such as a desktop computer and a smart TV in addition to various mobile devices such as a smartphone, a cellular phone, a tablet PC, a notebook, a netbook, a personal digital assistant (PDA), a portable multimedia player (PMP), a Play Station Portable (PSP), an MP3 player, an e-book reader, a navigation device, a smart camera, an electronic dictionary, an electronic watch, and a game console.

The device 10 may execute various applications on the basis of an operating system (OS). The OS is a system program for allowing an application to use a device's hardware and may include mobile computer operating systems such as iOS, Android OS, Window Mobile OS, Bada OS, Symbian OS, and Blackberry OS and computer operating systems such as Windows series, Linux series, Unix series, MAC, AIX, and HP-UX.

The application is a program that is developed to perform a specific task using a terminal, and may include various kinds of multimedia content such as games, videos, and photographs or execution programs such as an image viewer and a video player for executing the multimedia content, in addition to various kinds of application programs and service objects. It will be appreciated that the application may include all application programs and execution programs.

The effective frame detection unit 110 detects and outputs an effective frame of a user's input voice signal. The voice signal may be input to the device 10 either directly or over communication. That is, the voice signal may be input through a microphone included in the device 10 or may be transmitted from a remote location.

Figure 2:
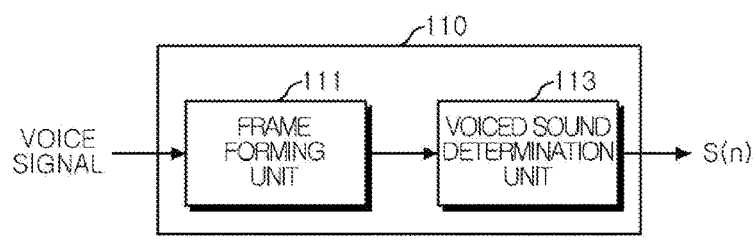
FIG. 2 is a detailed block diagram of an effective frame detection unit of FIG. 1.

Referring to FIG. 2, the effective frame detection unit 110 includes a frame forming unit 111 configured to form a voice frame of the input voice signal and a voiced sound determination unit 113 configured to determine whether the voice frame corresponds to a voiced sound.

The frame forming unit 111 receives a person's voice, converts the received voice into voice data, converts the voice data into voice frame data in units of frames, and outputs the voice frame data. Typically, analog voice signals are sampled at a rate of 8000 per second and in the size of 16 bits (65535 steps) and converted into voice data.

The frame forming unit 111 may convert a received voice signal into voice data and convert the voice data into voice frame data in units of frames. Here, one piece of the voice frame data has 256 energy values.

Figure 3:
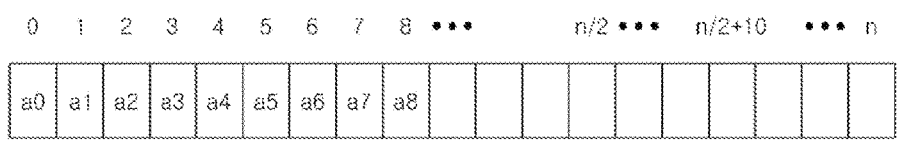
FIG. 3 is a view for describing a concept in which a frame forming unit of an effective frame detection unit of FIG. 2 converts a voice signal into a voice frame.

As shown in FIG. 3, the voice data is composed of a plurality of voice frames (n=the number of frames, n=1, 2, 3, . . . ) according to the received voice. The frame forming unit 111 generates a voice frame and then outputs information regarding the voice frame to the voiced sound determination unit 113.

The voiced sound determination unit 113 receives a voice frame, extracts predetermined features from the voice frame, and analyzes whether the received voice frame is associated with a voiced sound, an unvoiced sound, or noise according to the extracted features. According to a result of the analysis, the voiced sound determination unit 113 may separate only a frame corresponding to a voiced sound from the voice frames and output the separated frame.

Figure 4:
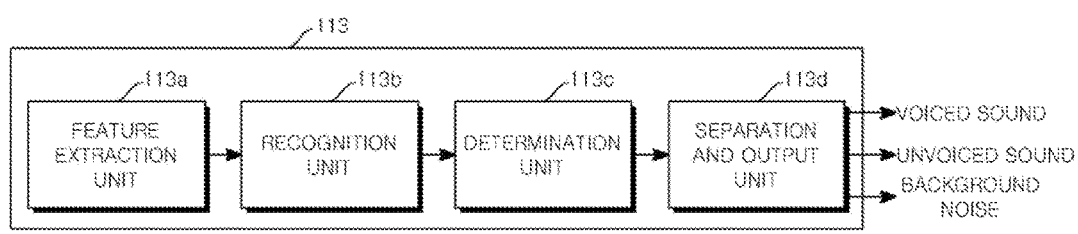
FIG. 4 is a detailed block diagram of a voiced sound determination unit of the effective frame detection unit of FIG. 2.

Referring to FIG. 4, the voiced sound determination unit 113 may include a feature extraction unit 113a configured to receive a voice frame and extract predetermined features from the voice frame, a recognition unit 113b configured to yield a recognition result for the voice frame, a determination unit 113c configured to determine whether the received voice frame is associated with a voiced sound or an unvoiced sound or whether the received voice frame is caused by background noise, and a separation and output unit 113d configured to separate and output an effective frame according to a result of the determination.

When the voice frame is received through the frame forming unit 111, the feature extraction unit 113a may extract, from the received voice frame, periodic characteristics of harmonics or features such as root mean square energy (RMSE) or zero-crossing count (ZC) of a low-band voice signal energy area.

Generally, the recognition unit 113b may be composed of a neural network. This is because the neural network is useful in analyzing non-linear problems (i.e., complicated problems that cannot be solved mathematically) and thus is suitable for analyzing voice signals and determining whether a corresponding voice signal is determined as a voiced signal, an unvoiced signal, or background noise according to a result of the analysis. The recognition unit 113b, which is composed of such a neural network, may assign predetermined weights to the features extracted from the feature extraction unit 113a and may yield a recognition result for the voice frame through a calculation process of the neural network. Here, the recognition result refers to a value that is obtained by calculating calculation elements according to the weights assigned to the features of each voice frame.

The determination unit 113c determines whether the received voice signal corresponds to a voiced sound or an unvoiced sound according to the above-described recognition result, that is, the value calculated by the recognition unit 113b. The separation and output unit 113d separates the voice frame as a voiced sound, an unvoiced sound, or background noise according to a result of the determination of the determination unit 113c.

Meanwhile, since the voiced sound is distinctly different from the voiced sound and the background noise in terms of various features, it is relatively easy to identify the voiced sound, and there are several well-known techniques for this. For example, the voiced sound has periodic characteristics in which harmonics are repeated at every certain frequency interval while the background noise does not have the harmonics.

On the other hand, the unvoiced sound has harmonics with weak periodicity. In other words, the voiced sound is characterized in that the harmonics are repeated within one frame while the unvoiced sound is characterized in that the characteristics of the voiced sound such as the harmonics are repeated every certain number of frames, that is, is shown to be weak.

When the voiced sound determination unit 113 separates a voiced sound, an unvoiced sound, or background noise, the effective frame detection unit 110 outputs only a frame for a voiced sound. The output frame for the voiced sound is referred to as an original signal S(n) of the effective frame, and the original signal S(n) of the effective frame is transferred to the difference signal detection unit 130.

Figure 5:
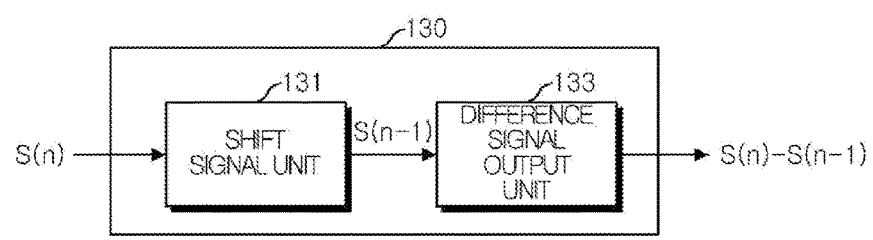
FIG. 5 is a detailed block diagram of a difference signal detection unit of FIG. 1.

Referring to FIG. 5, the difference signal detection unit 130 includes a shift signal unit 131 and a difference signal output unit 133 in order to output a difference signal S(n)–S(n–1) of the original signal S(n) of the effective frame.

The shift signal unit 131 generates a shift signal S(n–1) by shifting the original signal S(n) of the effective frame, and the difference signal output unit 133 outputs a difference signal S(n)–S(n–1) between the original signal and the shift signal S(n–1).

As features before and after drinking, it has been reported that high-frequency components increase like characteristics of a nasal sound. That is, there is a significant difference in high-frequency components while low-frequency components almost do not change. Drinking causes auditory degradation. Accordingly, a speaker should speak with a loud voice and thus open his or her mouth wide because the speaker would not be able to hear well. This increases the lung capacity and affects energy. In addition, when the speaker is drunk, the volume of their voice cannot be maintained and usually increases or decreases excessively. Accordingly, a deviation in the volume of the voice increases after drinking.

According to the present invention, a difference signal of an original signal is found. The found difference signal shows a characteristic that high-frequency components are highlighted. Therefore, the difference between before and after drinking may be further highlighted, and also a high-frequency analysis may be further facilitated by using the difference signal.

The Fourier transform unit 150 converts the voice signal into the frequency domain by performing a fast Fourier transform (FFT) on the difference signal S(n)–S(n–1) of the effective frame that is output from the difference signal detection unit 130.

The Fourier transform is a method of converting signals from the time domain to the frequency domain to analyze composite signals in order to find frequencies and characteristics of the signals. For example, when a signal is transmitted from an antenna, radio waves may be heard through frequency adjustment using a radio. It should be appreciated that the frequency adjustment serves as a filter for blocking signals (radio waves) with other frequencies. The Fourier transform is performed in order to make such a filter. The conversion of a time function u(t) into a frequency function U(w) is referred to as a Fourier transform, and the conversion of a frequency function U(w) into a time function u(t) is referred to as an inverse Fourier transform.

The fast Fourier transform is an algorithm that is designed to reduce the number of operations needed when a discrete Fourier transform using an approximation formula is performed on the basis of the Fourier transform.

The fast-Fourier-transformed difference signal FFT(S(n)–S(n–1)) is a voice signal in the frequency domain and is output to the high-frequency detection unit 170.

The high-frequency detection unit 170 detects and groups high-frequency components of the fast-Fourier-transformed difference signal. The present invention divides a change in voice for one frame into small units, measures a change in high frequency, and uses the measured change as a feature parameter.

In detail, the high-frequency detection unit 170 performs a fast Fourier transform on the difference signal to convert the difference signal into the frequency domain and then filtering the high-frequency components in units of a certain number to rearrange the high-frequency components. That is, the high-frequency components are sequentially grouped in sets of a certain number. Thus, low frequency components and high-frequency components are uniformly distributed.

Figure 6:
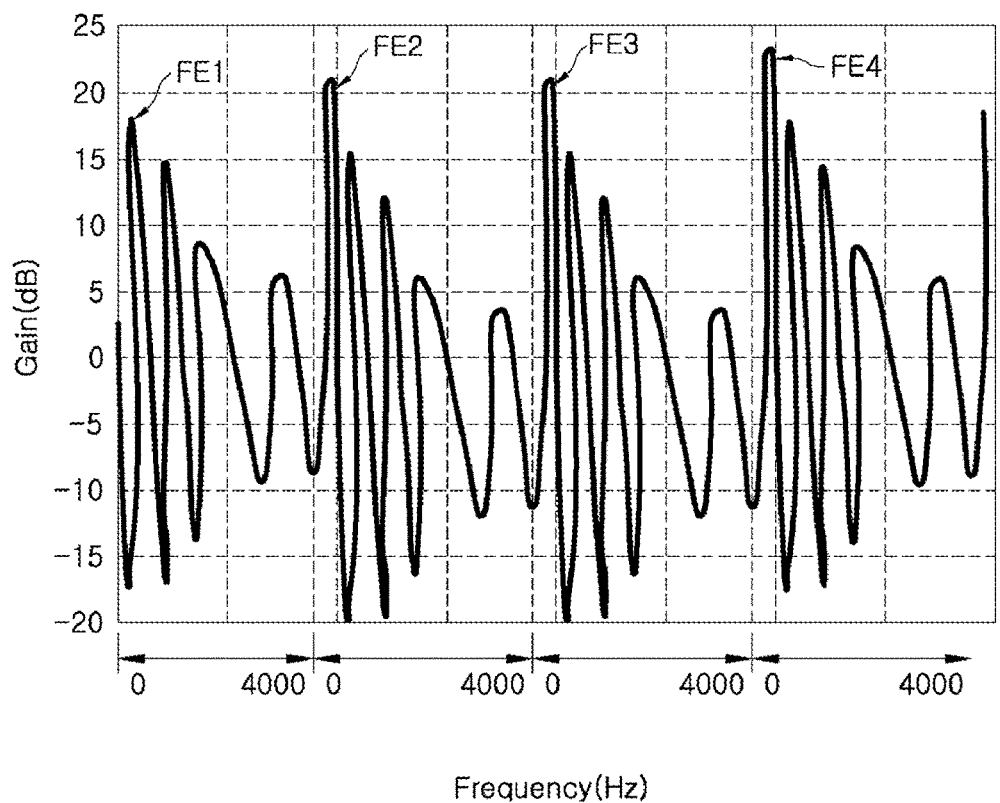
FIG. 6 is a graph for describing an example in which a high-frequency detection unit of FIG. 1 detects and groups high frequencies.

FIG. 6 shows first to fourth high-frequency components FE1, FE2, FE3, FE4. For example, when grouped in sets of four, FE1, FE2, FE3, FE4 form one group. This is the same effect as obtained when one frame is divided into four parts and a fast Fourier transform is performed on the four parts.

In this case, the high-frequency detection unit 170 may include a first high-frequency detection unit configured to detect the first, fifth, ninth, thirteenth, etc. high-frequency components of the fast-Fourier-transformed difference signal, a second high-frequency detection unit configured to detect the second, sixth, tenth, fourteenth, etc. high-frequency components of the fast-Fourier-transformed difference signal, a third high-frequency detection unit configured to detect the third, seventh, eleventh, fifteenth, etc. high-frequency components of the fast-Fourier-transformed difference signal, and a fourth high-frequency detection unit configured to detect the fourth, eighth, twelfth, sixteenth, etc. high-frequency components of the fast-Fourier-transformed difference signal.

The voice signal shows large variations in the high-frequency components of 2 kHz or higher before and after drinking. The present invention is characterized in that a change in the high-frequency component may be analyzed in a short time. Therefore, according to the present invention, a short-term feature may be analyzed by using the characteristic.

The detected high-frequency components FE1, FE2, FE3, and FE4 are output to the alcohol consumption determination unit 190.

The alcohol consumption determination unit 190 finds an energy difference from the high-frequency components FE1, FE2, FE3, and FE4 in one group and determines whether alcohol has been consumed. In order to find energy differences among the high-frequency components, the alcohol consumption determination unit 190 may generate slopes of the high-frequency components and yield the energy differences from differences among the slopes.

When a person is drunk, his or her ability to control the volume of his or her voice is reduced, resulting in an increased energy change of a high-frequency component. Thus, the alcohol consumption determination unit 190 may determine whether alcohol has been consumed according to a difference of the energy change of the high-frequency component during a certain period.

Figure 7:
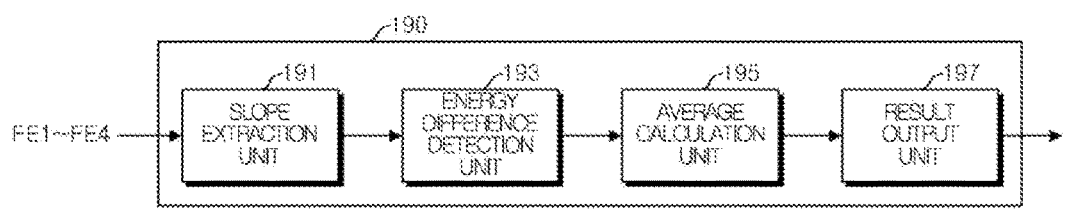
FIG. 7 is a detailed block diagram of an alcohol consumption determination unit of FIG. 1.

Referring to FIG. 7, the alcohol consumption determination unit 190 includes a slope extraction unit 191, an energy difference detection unit 193, an average calculation unit 195, and a result output unit 197.

The slope extraction unit 191 generates frequency slopes of the high-frequency components FE1, FE2, FE3, and FE4. Each of the frequency slopes may be a formant slope.

Figure 8:
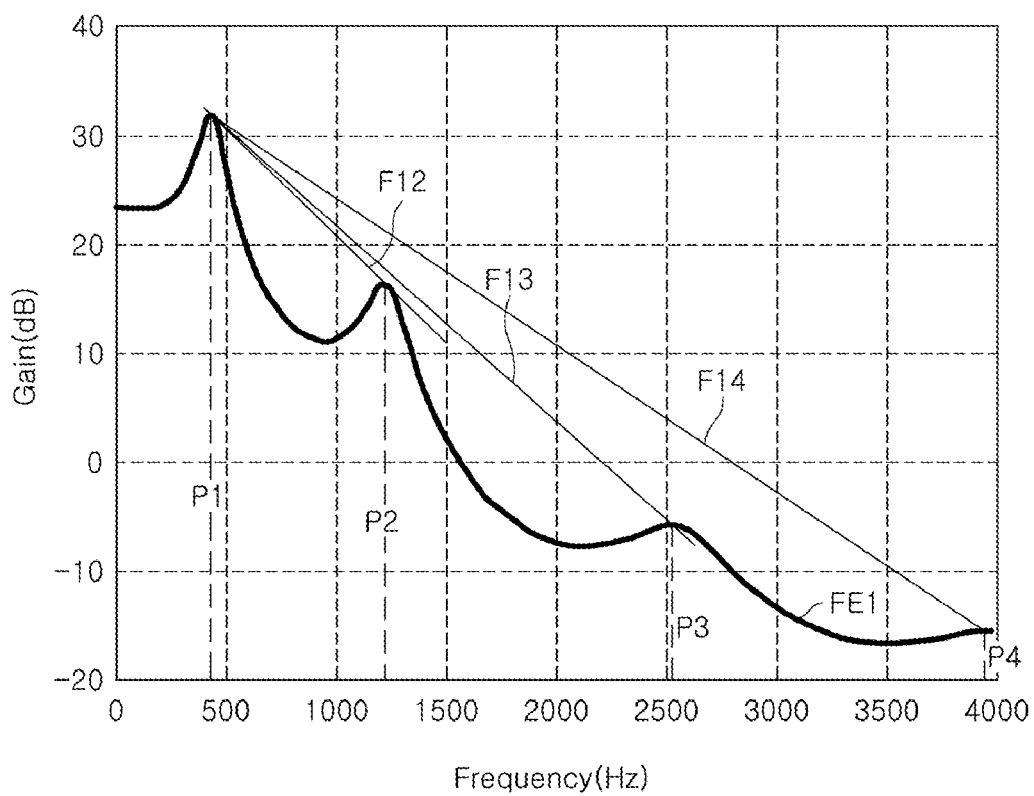
FIG. 8 is a graph showing a formant slope generated by an alcohol consumption determination unit of FIG. 1.

FIG. 8 shows that a formant slope is extracted from the first high-frequency component FE1. The first high-frequency component FE1 is a frequency domain signal. In this case, first to fourth peak frequencies P1, P2, P3, and P4 are found, starting with the lowest frequency peak.

The slope extraction unit 191 may extract a slope F14 between the first peak frequency P1 and the fourth peak frequency P4, a slope F13 between the first peak frequency P1 and the third peak frequency P3, a slope F12 between the first peak frequency P1 and the second peak frequency P2, etc.

For example, F14 (a slope between the first peak frequency and the fourth peak frequency) and F24 (a slope between the second peak frequency and the fourth peak frequency) among a plurality of formant slopes may be used to determine whether alcohol has been consumed. After a person drinks alcohol, his or her ability to control the volume of his or her voice is reduced due to a physical change. Thus, since the person cannot talk smoothly and rhythmically by using a change in energy, the person makes consecutive pronunciations with a loud voice or makes pronunciations with a loud voice even when the pronunciation should be made with a low voice. This feature denotes that a change occurs in the first peak frequency P1 Furthermore, tongue position is changed upon pronunciation when alcohol has been consumed. This affects the second peak frequency P2. That is, the second peak frequency P2 increases when the tongue is positioned forward and decreases when the tongue is positioned backward. The fourth peak frequency P4 is hardly affected by an articulator, and thus is almost constant before and after drinking. Accordingly, whether alcohol has been consumed may be more easily determined according to the variations of F14 and F24.

The slope extraction unit 191 extracts formant slopes from the second to fourth high-frequency components FE2 to FE4 in the same method and output the extracted formant slopes to the energy difference detection unit 193.

The energy difference detection unit 193 measure slope differences among high-frequency components in one group to measure energy differences among the high-frequency components. The energy differences may result from distance differences among the formant slopes.

For example, the energy difference detection unit 193 may measure slope differences among neighboring high-frequency components. That is, the energy difference detection unit 193 may find a slope difference between the first high-frequency component FE1 and the second high-frequency component FE2, a slope difference between the second high-frequency component FE2 and the third high-frequency component FE3, and a slope difference between the third high-frequency component FE3 and the fourth high-frequency component FE4.

However, in another embodiment, the energy difference detection unit 193 may further extract slope differences among non-neighboring high-frequency components. For example, the energy difference detection unit 193 may further measure a slope difference between the first high-frequency component FE1 and the third high-frequency component FE3, a slope difference between the second high-frequency component FE2 and the fourth high-frequency component FE4, a slope difference between the first high-frequency component FE1 and the fourth high-frequency component FE4, etc. to detect energy differences.

Figure 9:
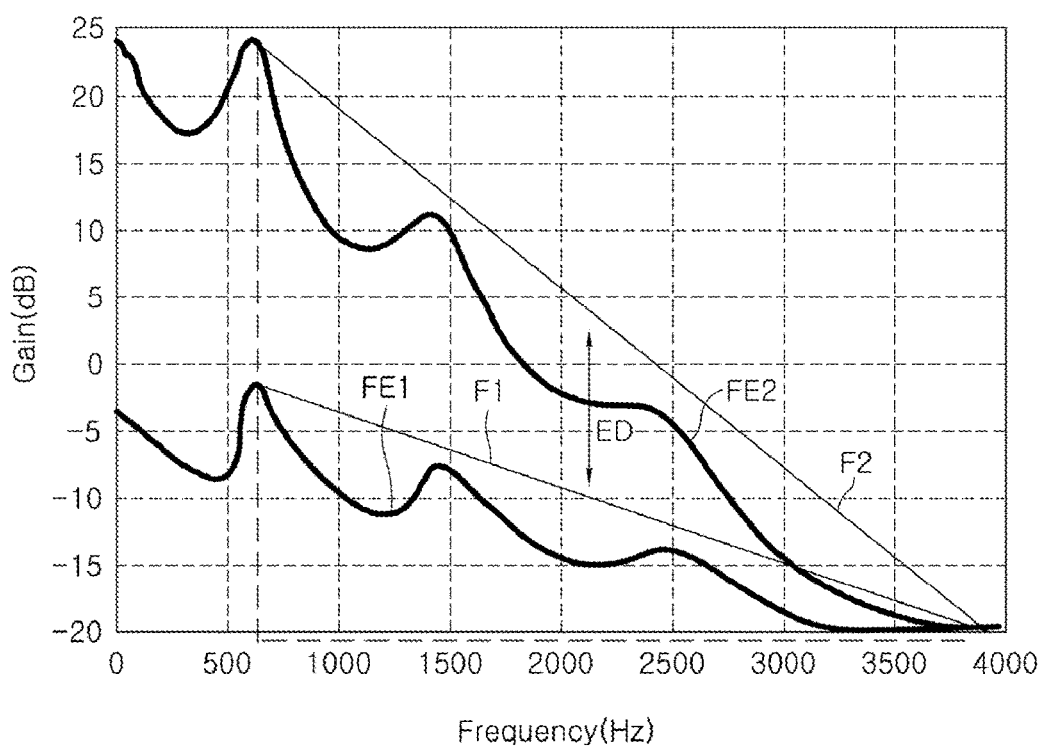
FIG. 9 is a graph showing an energy difference obtained by measuring a variation of slope using an alcohol consumption determination unit of FIG. 1.

Referring to FIG. 9, the energy difference detection unit 193 yields an energy difference ED from a formant slope difference between the first high-frequency component FE1 and the second high-frequency component FE2. The formant slope difference between a slope F1 of the fast-Fourier-transformed original signal FE1 and a slope F2 of the fast-Fourier-transformed difference signal FE2 is a distance difference between the slopes. Since the difference varies depending on the frequency, the energy difference detection unit 193 may calculate an average of the distance differences.

The energy difference detection unit 193 may detect an energy difference between the second high-frequency component FE2 and the third high-frequency component FE3 and an energy difference between the third high-frequency component FE3 and the fourth high-frequency component FE4 in the same method. The detected energy differences are provided to the average calculation unit 195.

The average calculation unit 195 adds up the measured energy differences to calculate an average of the energy differences and provides the calculated average to the result output unit 197. On a condition that there are two or more groups, the average calculation unit 195 finds energy differences among high-frequency components in one group and adds up energy differences in all of the groups to calculate an energy average.

The result output unit 197 may determine that alcohol has been consumed when the average of the energy differences is greater than a threshold and may determine that alcohol has not been consumed when the average is less than or equal to the threshold.

The threshold may be predetermined and stored and also may be applied in all cases. The threshold may be an optimal value that is set experimentally. Different thresholds may be applied depending on gender or age or according to customization.

The alcohol consumption determination device according to the present invention determines whether alcohol has been consumed in the frequency domain. In particular, the alcohol consumption determination device utilizes a formant energy comparison method in the frequency domain in order to highlight high frequencies of the voice signal and also increase analysis accuracy for the signal. In addition, the alcohol consumption determination device according to the present invention may divide a change in voice for one frame into small units, measures a change in high frequency, and uses the measured change as a feature parameter. Thus, a change in high frequency component may be analyzed in short time. Accordingly, this is an analysis method that is useful in determining whether alcohol has been consumed and a degree of the consumption by analyzing features of the short term.

Figure 10:
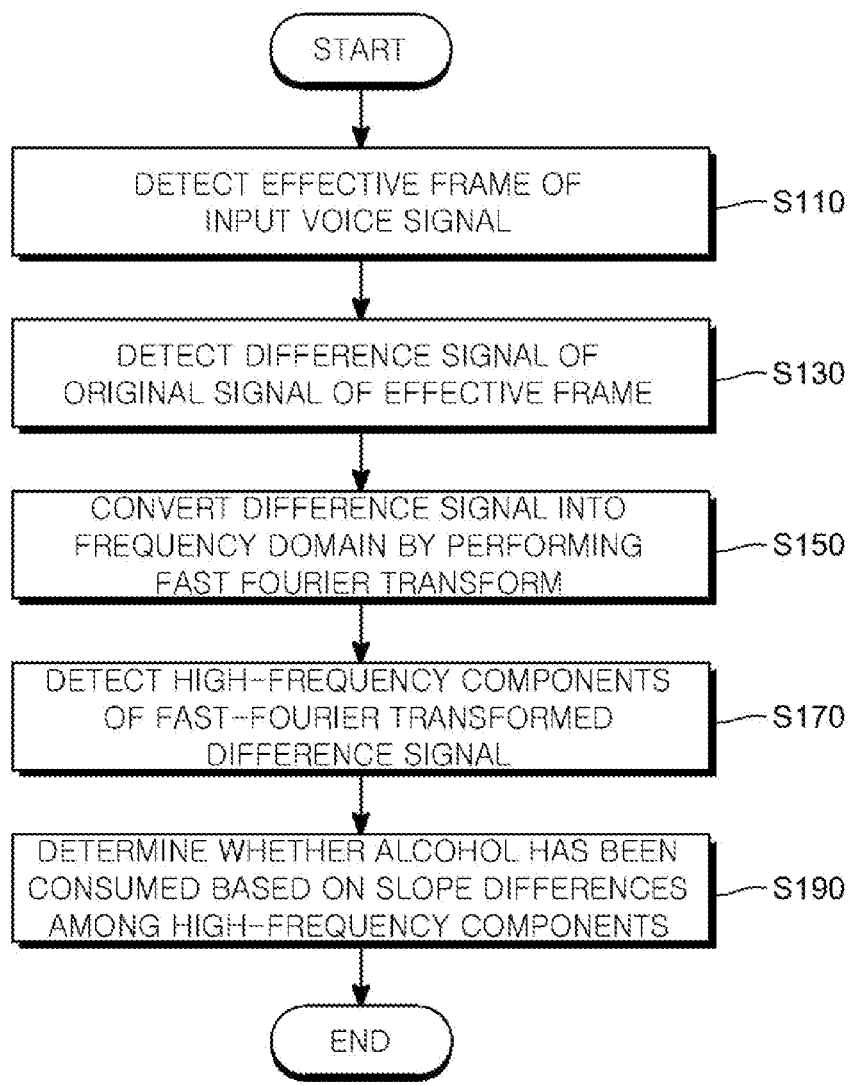
FIG. 10 is a flowchart showing an alcohol consumption determination method according to an embodiment of the present invention.

FIG. 10 is a flowchart showing an alcohol consumption determination method according to an embodiment of the present invention.

The alcohol consumption determination method according to this embodiment may be performed in substantially the same configuration as that of the device 10 of FIG. 1. Therefore, the same elements as those of the device 10 of FIG. 1 are designated by the same reference numerals, and repetitive descriptions thereof will be omitted.

Alternatively, the alcohol consumption determination method according to this embodiment may be executed by alcohol consumption determination software (application).

Referring to FIG. 10, the alcohol consumption determination method according to this embodiment includes detecting an effective frame of an input voice signal (step S110).

The step of detecting the effective frame (step S110) may include forming a voice frame of the input voice signal and determining whether the voice frame corresponds to a voiced sound.

In detail, the step may include receiving a person's voice, converting the voice into voice data, converting the voice data into voice frame data in units of a frame, and analyzing whether the voice frame is associated with a voiced sound, an unvoiced sound, or noise. According to a result of the analysis, only a frame corresponding to a voiced sound, that is, an effective frame may be output.

The method includes detecting a difference signal of an original signal of the effective frame when the effective frame is detected (step S130).

The step of detecting the difference signal (step S130) may include generating a shift signal S(n−1) by shifting the original signal S(n) of the effective frame and outputting a difference signal S(n)−S(n−1) between the original signal and the shift signal.

Since the difference signal shows a characteristic that high-frequency components are highlighted, the difference between before and after drinking may be further highlighted, and also the analysis of high frequencies may be further facilitated by using the difference signal.

The method includes converting the difference signal into the frequency domain by performing a fast Fourier transform on the difference signal (step S150).

The method includes detecting high-frequency components of the fast-Fourier-transformed difference signal (step S170).

The step of detecting high-frequency components (step S170) may include sequentially grouping the detected high-frequency components in sets of four.

The method includes determining whether alcohol has been consumed on the basis of slope differences among the high-frequency components (step S190).

The step of determining whether alcohol has been consumed (step S190) may include generating frequency slopes of the high-frequency components, measuring slope differences among the high-frequency components to measure energy differences among the high-frequency components, adding up the measured energy differences to calculate an average of the energy differences, and determining that alcohol has been consumed when the average is greater than a threshold and outputting a result of the determination.

Each of the frequency slopes of the high-frequency components may be a formant slope. A difference between the formant slopes is a distance difference between the slopes. Since the difference varies depending on the frequency, an average of the distance differences may be calculated. By the same method, energy differences between neighboring high-frequency waves are detected, and an average of the energy differences is calculated.

When the average of the energy differences is greater than the threshold, a change in energy of the high-frequency component is large. Accordingly, it may be determined that alcohol has been consumed.

As described above, the alcohol consumption determination method may be implemented as an application or implemented in the form of program instructions that may be executed through various computer components and recorded on a computer-readable recording medium. The computer-readable recording medium may include program instructions, data files, data structures, and the like individually or in combination.

The program instructions recorded on the computer-readable recording medium may be specifically designed for the present invention or may be well-known to and used by those skilled in the art of computer software.

Examples of the computer-readable recording medium include a magnetic medium such as a hard disk, a floppy disk, or a magnetic tape, an optical medium such as a compact disc-read only memory (CD-ROM) or a digital versatile disc (DVD), a magneto-optical medium such as a floptical disk, and a hardware device such as a ROM, a random access memory (RAM), or a flash memory that is specially designed to store and execute program instructions.

Examples of the program instructions include not only machine code generated by a compiler or the like but also high-level language codes that may be executed by a computer using an interpreter or the like. The hardware device may be configured to operate as one or more software modules in order to perform operations of the present invention, and vice versa.

Although the present invention has been described with reference to exemplary embodiments, it will be understood that various changes and modifications may be made herein without departing from the scope and spirit of the present invention defined in the appended claims.

INDUSTRIAL APPLICABILITY

The alcohol consumption determination method according to the present invention and the recording medium and device for implementing the same may determine whether a driver or operator at a remote location has consumed alcohol through communication, thus preventing an accident caused by an individual operating a vehicle under the influence. In addition, the present invention may be widely applied to transportation areas such as vessels, rail roads, aircrafts, vehicles, buses, and highways in which it is difficult to measure alcohol consumption in person and also to domestic and foreign systems of vessels and air control services. Furthermore, the present invention may contribute to a web application on a personal cellular phone for measuring alcohol consumption.

The invention claimed is:

1. A computer implemented method for determining whether alcohol is consumed by a person by using at least one processor for executing a specific computer software to perform steps comprising:
receiving an input voice signal from said person via a microphone sensor;
forming an effective frame by converting the input voice signal from said person;
forming a voice frame of the input voice signal from said person;
determining whether the formed voice frame corresponds to a voiced sound;
generating an original signal of the formed effective frame and a difference signal of the original signal, which is a difference between the original signal of the formed effective frame and a shift signal thereof;
converting the difference signal into a frequency domain signal by performing a fast Fourier transform algorithm on the difference signal;
detecting high-frequency components of the fast-Fourier-transformed difference signal; and
determining whether alcohol is consumed by said person based on slope differences among the high-frequency components; and
outputting a result of a determination whether alcohol is consumed by said person who is located in a remoted area.

2. The computer implemented method of claim 1, wherein the determining whether the formed voice frame corresponds to the voiced sound comprises:
extracting periodic characteristics of harmonics or features from the formed voice frame, and determining whether the formed voice frame is from the voiced sound, an unvoiced sound, or background noise based on the extracted periodic characteristics of harmonics or features.

3. The computer implemented method of claim 2, wherein periodic characteristics of harmonics or features comprise root mean square energy (RMSE) or zero-crossing count (ZC) of a low-band voice signal energy area.

4. The computer implemented method of claim 2, wherein the determining whether the formed voice frame is from the voiced sound, an unvoiced sound, or background noise based on the extracted periodic characteristics of harmonics or features comprises use of neural network.

5. The computer implemented method of claim 1, wherein the generating the original signal of the formed effective frame and the difference signal of the original signal comprises:
   generating the original signal S(n) of the formed effective frame;
   generating the shift signal S(n−1) by shifting the original signal S(n); and
   generating the difference signal S(n)−S(n−1) between the original signal S(n) and the shift signal S(n−1).

6. The computer implemented method of claim 5, wherein the difference signal S(n)−S(n−1) comprises a characteristic of highlighting high-frequency components.

7. The computer implemented method of claim 1, wherein the detecting of high-frequency components of the fast-Fourier-transformed difference signal comprises sequentially grouping the detected high-frequency components in sets of four.

8. The computer implemented method of claim 1, wherein the determining whether said person is drunk based on slope differences comprises:
   generating frequency slopes of the high-frequency components;
   measuring energy differences among the high-frequency components by computing slope differences among the high-frequency components;
   calculating an average of the energy differences by adding up the measured energy differences; and
   determining that said person is drunk when the calculated average of the energy differences is greater than a threshold and outputting a result of the determination.

9. The computer implemented method of claim 8, wherein each of the frequency slopes of the high-frequency components is a formant slope.

10. The computer implemented method of claim 9, wherein the measuring energy differences among the high-frequency components by computing slope differences among the high-frequency components comprises computing slope differences among neighboring high-frequency components.

11. A non-transitory computer-readable recording medium having the specific computer software recorded thereon for performing a method comprising:
   receiving an input voice signal from said person via a microphone sensor;
   forming an effective frame by converting the input voice signal from said person;
   forming a voice frame of the input voice signal from said person;
   determining whether the formed voice frame corresponds to a voiced sound;
   generating an original signal of the formed effective frame and a difference signal of the original signal, which is a difference between the original signal of the formed effective frame and a shift signal thereof;
   converting the difference signal into a frequency domain signal by performing a fast Fourier transform algorithm on the difference signal;
   detecting high-frequency components of the fast-Fourier-transformed difference signal;
   determining whether alcohol is consumed by said person based on slope differences among the high-frequency components; and
   outputting a result of a determination whether alcohol is consumed by said person who is located in a remoted area.

12. The non-transitory computer-readable recording medium of claim 11, wherein the determining whether the formed voice frame corresponds to the voiced sound comprises:
   extracting periodic characteristics of harmonics or features from the formed voice frame, and
   determining whether the formed voice frame is from the voiced sound, an unvoiced sound, or background noise based on the extracted periodic characteristics of harmonics or features.

13. The non-transitory computer-readable recording medium of claim 12, wherein periodic characteristics of harmonics or features comprise root mean square energy (RMSE) or zero-crossing count (ZC) of a low-band voice signal energy area.

14. The non-transitory computer-readable recording medium of claim 12, wherein the determining whether the formed voice frame is from the voiced sound, an unvoiced sound, or background noise based on the extracted periodic characteristics of harmonics or features comprises use of neural network.

15. The non-transitory computer-readable recording medium of claim 11, wherein the generating the original signal of the formed effective frame and the difference signal of the original signal comprises:
   generating the original signal S(n) of the formed effective frame;
   generating the shift signal S(n−1) by shifting the original signal S(n); and
   generating the difference signal S(n)−S(n−1) between the original signal S(n) and the shift signal S(n−1).

16. The non-transitory computer-readable recording medium of claim 15, wherein the difference signal S(n)−S(n−1) comprises a characteristic of highlighting high-frequency components.

17. The non-transitory computer-readable recording medium of claim 11, wherein the detecting of high-frequency components of the fast-Fourier-transformed difference signal comprises sequentially grouping the detected high-frequency components in sets of four.

18. The non-transitory computer-readable recording medium of claim 11, wherein the determining whether said person is drunk based on slope differences comprises:
   generating frequency slopes of the high-frequency components;
   measuring energy differences among the high-frequency components by computing slope differences among the high-frequency components;
   calculating an average of the energy differences by adding up the measured energy differences; and
   determining that said person is drunk when the calculated average of the energy differences is greater than a threshold and outputting a result of the determination.

19. The non-transitory computer-readable recording medium of claim 18, wherein each of the frequency slopes of the high-frequency components is a formant slope.

20. The non-transitory computer-readable recording medium of claim 19, wherein the measuring energy differences among the high-frequency components by computing slope differences among the high-frequency components comprises computing slope differences among neighboring high-frequency components.

* * * * *